United States Patent [19]
Capdevila et al.

[11] Patent Number: 5,834,293
[45] Date of Patent: Nov. 10, 1998

[54] CYTOCHROME P450 ARACHIDONIC ACID EPOXYGENASE GENETIC MUTATION ASSOCIATED WITH HYPERTENSION

[75] Inventors: Jorge H. Capdevila; Keiko Makita, both of Nashville, Tenn.; Armando Karara, Buenos Aires, Argentina

[73] Assignee: Vanderbilt University, Nashville, Tenn.

[21] Appl. No.: 314,601

[22] Filed: Sep. 28, 1994

[51] Int. Cl.$^6$ ............... C12N 5/00; C12N 15/63; C07H 21/00
[52] U.S. Cl. .................. 435/240.2; 435/240.2; 435/172.3; 435/6; 935/70; 935/77; 935/78; 536/23.1
[58] Field of Search ............. 536/23.1; 435/240.2, 435/172.3, 6; 935/70, 77, 78

[56] References Cited

U.S. PATENT DOCUMENTS 5,508,199  4/1996  Gonzalez et al. .............. 435/320.1

OTHER PUBLICATIONS deMorais et al. "The Major Genetic Defect Responsible for the Polymorphism . . ." *J. Biol. Chem.* 269(22):15419–15422, Jun. 1994.
Nelson et al. "The P450 Superfamily:Update on New Sequences . . . " *DNA and Cell Biol.* 12(1):1–51, 1993.
Karara et al. "Molecular Cloning, Expression, and Enzymatic Charcterization . . . " *J. Biol. Chem.* 268(18):13565–13570, Jun., 1993.
Capdevila et al. "Cytochrome P450 and the Arachidonate Cascade" *FASEB J.* 6:731–736, 1992.
Capedevila et al. "Cytochrome P–450 Arachidonic Acid Epoxygenase" *J. Biol. Chem.* 267(30):21720–21726, 1992.
Okino et al. "Characterization of Multiple Human Cytochrome P–450 1 cDNAs" *J. Biol. Chem.* 262(33):16072–16079, 1987.
Morishima et al., Biochemistry 26 : 8279–8285 (1987).
Rapp et al., Science 243 : 542–544 (1989).
Romkes et al., Biochemistry 30 : 3247–3255 (1991).
Meehan et al., Am. J. Hum. Genet. 42 : 26–37 (1988).

*Primary Examiner*—Jasemin C. Chambers
*Assistant Examiner*—Karen M. Hauda
*Attorney, Agent, or Firm*—Needle & Rosenberg, P.C.

[57] ABSTRACT

The invention provides an isolated nucleic acid encoding the rat P450 2C11 arachidonic acid epoxygenase, or a human homologue thereof, having a mutation associated with salt induced hypertension. Also provided is an isolated cell line expressing the epoxygenase encoded by the mutated nucleic acid, and a non-human transgenic animal having a germ line insertion of the mutated nucleic acid. Also provided is a method of screening a compound for efficacy in treating salt induced hypertension comprising administering the compound to such a non-human transgenic animal, and detecting an improvement in the animal's hypertension. The invention also provides a method of screening a human subject for a genetic predisposition to salt induced hypertension comprising detecting a mutation in a human homologue of a rat P450 2C11 arachidonic acid epoxygenase gene which affects normal epoxygenase activity. Also provided is a method of treating salt induced hypertension in a human subject associated with a genetic mutation in a human homologue of the rat P450 2C11 arachidonic acid epoxygenase gene, comprising administering to the subject a functional metabolite, or analogue thereof, produced by the human homologue of the rat P450 2C11 arachidonic acid epoxygenase. Also provided is an isolated mutated rat P450 2C11 arachidonic acid epoxygenase, or a human homologue thereof, having a mutation associated with salt induced hypertension.

3 Claims, 6 Drawing Sheets

CYTOCHROME P450 ARACHIDONIC ACID EPOXYGENASE GENETIC MUTATION ASSOCIATED WITH HYPERTENSION

This work was supported in part by United States Public Health Services Grant NIHDK 38226. The United States Government has rights in the invention.

FIELD OF THE INVENTION

This invention relates to a mutation in a gene encoding Cytochrome P450 arachidonic acid epoxygenase which is associated with salt induced hypertension. The invention also relates to methods of detecting said mutation and methods of treatment of individuals afflicted with said mutation.

BACKGROUND ART

As the precursor for prostanoid biosynthesis, arachidonic acid (AA) serves multiple and important roles in renal physiology (1,2). Studies from several laboratories have demonstrated that metabolism of this fatty acid by microsomal Cytochrome P450 generates bioactive molecules which may also be of importance to kidney function (1,3,4). The microsomal Cytochrome P450 AA epoxygenase catalyzes the NADPH-dependent metabolism of the fatty acid to a mixture of 5,6-; 8,9-; 11,12-; and 14,15-cis-epoxyeicosatrienoic acids (EETs) (3,4). The regio- and stereochemical selectivity of the AA epoxygenase is P450 isoform specific (3) and, at difference with cyclooxygenase and lipoxygenase enzymes of the arachidonate cascade, variable and more or less tissue specific (3). The demonstration that P450 participates in the in vivo metabolism of endogenous AA pools, established the epoxygenase as a member of the arachidonate cascade and suggested a functional role for the hemoprotein in the generation of bioactive eicosanoids (3).

The potent biological activities associated with several EETs has stimulated interest in defining the role that the AA epoxygenase may play in renal physiology (1,3,4). Thus, the EETs or their hydration products, the DHETs, have been shown to alter tubular Na+ and K+ fluxes (6,7), water permeability (8,9) and, to be potent systemic vasodilators (1) and enantioselective intrarenal vasoconstrictors (10). Studies with the spontaneously hypertensive rat model (1), as well as marked changes in the urinary concentration of epoxygenase metabolites during pregnancy induced hypertension (11) suggested that this pathway may be of importance for the pathophysiology of hypertension. These studies, as well as the early observation of an inhibition of cortical Na+ reabsorption by 5,6-EET (6), prompted us to investigate the effects of dietary salt in the regulation of the renal epoxygenase(s).

In rats, excess dietary salt results in marked and selective increases in kidney epoxygenase activity with no significant changes in the microsomal AA ω/ω-1 oxygenase (5). Rat kidney microsomal fractions catalyze the highly asymmetric epoxidation of AA to a mixture of 8(R),9(S)-; 11(R),12(S)-; and 14(S),15(R)-EET (with optical purities of 95, 85, and 75%, respectively) (5). Importantly, the in vivo significance of these observations was established by the demonstration of a salt dependent 10–20 fold increase in the urinary output of epoxygenase metabolites (5). Antibody inhibition experiments indicated that the predominant epoxygenase isoform (s) present in rat kidney microsomal fractions belongs to the hemoprotein 2C gene subfamily (5). Immunoblotting studies demonstrated that excess dietary salt increased the rat kidney concentration of a P450 isoform(s) recognized by polyclonal antibodies raised against human liver P450 2C10 or rat liver P450 2C11 (5).

The P450 supergene family is characterized by an increasing complexity of isoforms coded for by unique genes that, in many cases, share extensive sequence homology (15,18). However, despite high degrees of homology, several isoforms display substantial catalytic diversity (18–22). In rats, the P450 2C gene subfamily is composed of 8 known members (15). Two of these isoforms are sex specific (P450 2C11 and 2C12) (15,18–22). P450s 2C6, 2C7, 2C11, 2C13, 2C22, 2C23 and 2C24 are all expressed in rat liver, with P450 2C11 as the predominant liver 2C isoform (18–23). Among the rat 2C subfamily proteins, P450 2C11, purified from rat liver, and recombinant P450 2C23 have been shown to actively catalyze arachidonic acid epoxygenation (24–26). The limited P450 2C isoform heterogeneity of the rat kidney was illustrated by the expression, at levels detectable by nucleic acid hybridization techniques and, in order of decreasing relative abundance, of only cytochromes 2C23, 2C24 and 2C11 (25,27).

P450 2C11, a male specific rat 2C gene subfamily isoform (19–22), is expressed predominantly in rat liver at levels that are regulated by age and hormones such as growth hormone, thyroid and steroids (19–22). Female rats express a female specific isoform, P450 2C12, which shows high sequence identity to 2C11 (20). Reconstitution studies utilizing solubilized and purified rat liver P450 2C11 demonstrated that this protein actively catalyzed the NADPH dependent epoxidation of AA (24). The presence of P450 2C11 mRNA transcripts in the rat kidney has been shown (25). Additionally, preliminary studies indicate that P450 2C11 expression may be highly localized to the juxtaglomerular section of the rat nephron. Although, the relative concentrations of P450 2C11 transcripts in the rat kidney are substantially lower than those coding for P450 2C23, it is important to note that the poly(A)$^+$RNAs utilized were isolated from whole kidneys and that, this approach does not take into account the known anatomical, functional and biochemical segmentation of the rat kidney. The rat P450 2C11 gene has been cloned and its exon/intron structure published (16). The gene is approximately 45 kb long and composed of 8 introns and 9 exons (16). FIG. 3 shows a map of the published intron/exon organization for the rat P450 2C11 gene. SEQ ID NO:1 shows the nucleic acid sequence of the normally expressed rat Cytochrome P450 2C11 gene and SEQ ID NO:2 shows the normally expressed amino acid sequence of rat Cytochrome P450 2C11.

A role for microsomal P450 in the pathophysiology of hypertension was initially proposed by McGiff and collaborators (1). Studies with the spontaneous hypertensive rat model (SHR/WKY model) indicated that, in these animals, the developmental phase of hypertension was associated with alterations in the activities of the microsomal P450 AA monooxygenase(s) (1,28,29). More recently, the significance of this proposal to human hypertension was suggested by the demonstration of marked increases in the urinary excretion of epoxygenase metabolites during pregnancy-induced hypertension (11).

The Dahl rat model of genetic salt dependent hypertension was developed from wild-type Sprague-Dawley (SD) stocks by selective breeding techniques (12). In these animals, genetic alterations in Na+ metabolism lead to systemic hypertension. After two to three weeks in a high salt diet, Dahl salt-sensitive (DS) animals develop high blood pressure. However, under similar conditions, Dahl salt-resistant (DR) animals remain essentially normotensive.

While in these animals, as in humans, hypertension was thought to be a polygenetic trait, transplantation studies clearly demonstrated that the kidney genotype played a pivotal role in the blood pressure response to increased dietary salt (13).

In previous studies it has been demonstrated that: a) in SD rats, Clotrimazole inhibition of the renal arachidonic acid epoxygenase results in the development of salt dependent hypertension and, b) at difference with normal SD or DR animals, DS rats are unable to induce their kidney arachidonic acid epoxygenase in response to dietary salt loading (5,14). SD and DR animals respond to excess dietary salt with marked increases in their water intake, urine volume and Na+ urinary excretion. This efficient adaptive response prevents Na+ retention, volume expansion and the development of systemic hypertension.

Researchers have also demonstrated that polyclonal antibodies raised against purified rat liver P450 2C11 immunoreact with the rat kidney P450 isoform(s) induced after dietary salt loading (5). However, stereochemical considerations have suggested that the molecular properties and the identity of the various isoform(s) induced in the rat kidney by excess dietary salt remain to be established. Several phenotypic and/or genotypic defects have been associated with the Dahl DR and DS phenotypes, including altered renal hemodynamics, prostanoid biosynthesis (31,32) and dopamine regulation of ion transport (33), as well as mutations in the genes coding for Na+/K+ ATPases (34, 35), mineralocorticoid biosynthesis (30,36) and renin (37). However, since none of these factors fully accounts for the differences in salt sensitivity observed between DS and DR animals, the genetic basis of salt sensitive hypertension in the Dahl rat remains unidentified.

The significance of the epoxygenase enzyme system to the functional differences in the response of the DR and DS genotypes to salt loading were characterized by DNA restriction fragment length polymorphism analysis, herein. To provide a molecular basis for the understanding of the role of the P450 arachidonic acid epoxygenase in renal function, genomic DNA from the livers of salt treated normotensive DR and hypertensive DS rats was isolated and analyzed by restriction endonuclease digestion and nucleic acid hybridization techniques. The data of the present invention shows that the Dahl salt sensitive phenotype is associated with structural differences in a P450 2C gene that codes for an arachidonic acid epoxygenase isoform. The existence of a polymorphism in the structure of the gene coding for a P450 2C11 AA epoxygenase in the Dahl rat model of salt sensitive hypertension is disclosed.

This genetic polymorphism appears to be caused by the loss of DNA fragment from a region of the DS rat 2C11 gene that maps between the gene exons 5 and 7. The documented 2C11 polymorphism may be associated with the inability of DS rats to up regulate their renal AA epoxygenase activity during salt loading. These results, in conjunction with: a) the demonstration that the epoxygenase metabolites are endogenous constituents of rat kidney and urine, b) the upregulation of the renal AA epoxygenase in SD and DR rats by excess dietary salt and, c) the potent biological activity of the EETs as inhibitors of distal Na+ reabsorption, demonstrate a role for the P450 AA epoxygenase in the pathophysiology of hypertension.

SUMMARY OF THE INVENTION

The invention provides an isolated nucleic acid encoding the rat P450 2C11 arachidonic acid epoxygenase, or a human homologue thereof, having a mutation associated with salt induced hypertension. Also provided is an isolated cell line expressing the epoxygenase encoded by the mutated nucleic acid, and a non-human transgenic animal having a germ line insertion of the mutated nucleic acid. Also provided is a method of screening a compound for efficacy in treating salt induced hypertension comprising administering the compound to such a non-human transgenic animal, and detecting an improvement in the animal's hypertension, thereby detecting a compound with efficacy in treating hypertension.

The invention also provides a method of screening a human subject for a genetic predisposition to salt induced hypertension comprising detecting a mutation in a human homologue of a rat P450 2C11 arachidonic acid epoxygenase gene which affects normal epoxygenase activity, the presence of the mutation indicating a predisposition to salt induced hypertension. Also provided is a method of treating salt induced hypertension in a human subject associated with a genetic mutation in a human homologue of the rat P450 2C11 arachidonic acid epoxygenase gene, comprising administering to the subject a functional metabolite, or analogue thereof, produced by the human homologue of the rat P450 2C11 arachidonic acid epoxygenase, thereby treating the salt induced hypertension. Also provided is an isolated mutated rat P450 2C11 arachidonic acid epoxygenase, or a human homologue thereof, having a mutation associated with salt induced hypertension.

Figure 3:
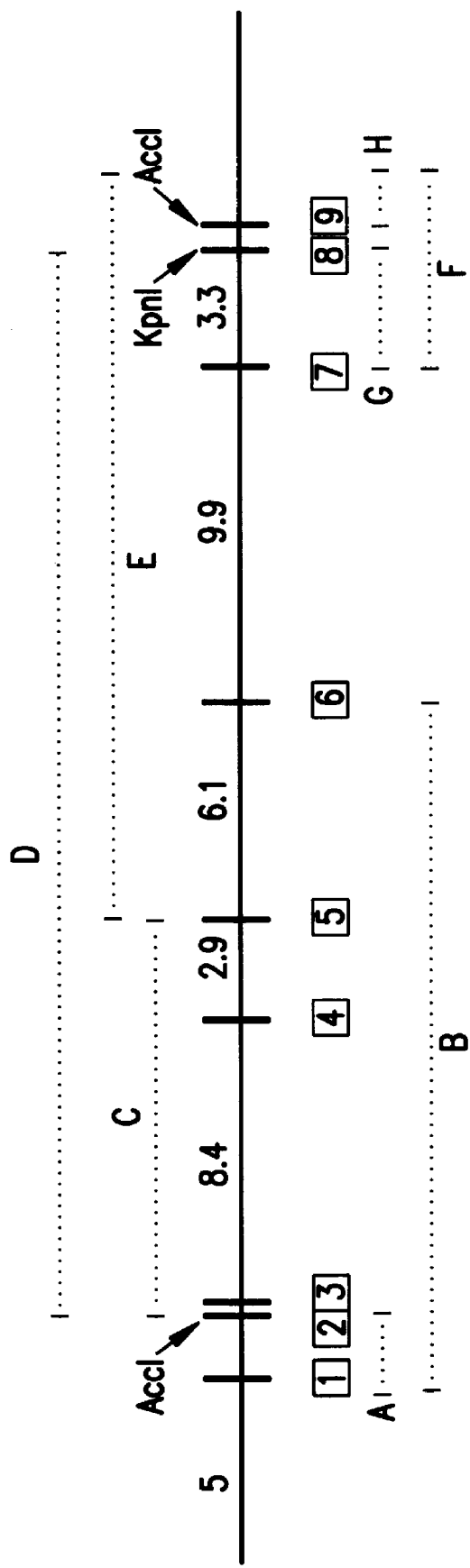
FIG. 3 Exon-intron organization of the rat P450 2C11 gene. The structural organization of the rat P450 2C11 gene presented in this Figure was adapted from reference 16. The P450 2C11 gene is composed of 9 exons (labeled 1 through 9 in the Figure) separated by 8 introns. Intron sizes are indicated in kilobase pairs. Shown in the Figure are: a) the relative position of the known exonic AccI and KpnI restriction sites (15–17) and, b) segments of the P450 2C11 gene (A through H) capable of hybridizing to selected probes generated by restriction endonuclease digestion of a 1.8 kb P450 2C11 cDNA (dotted lines).
Figure 4:
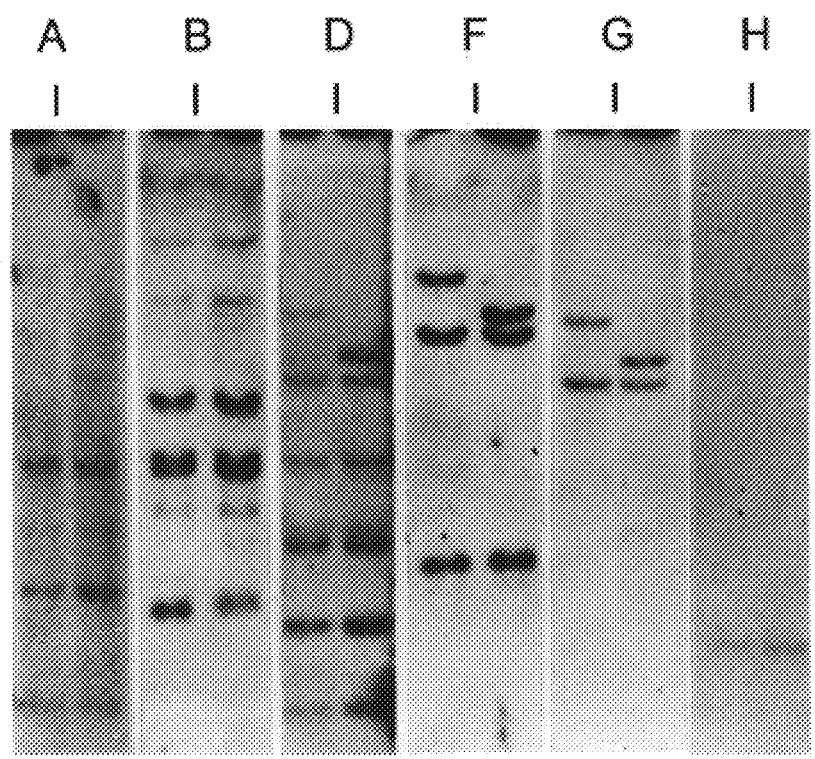
FIG. 4 Analysis of the hybridization patterns resulting from the interaction between AccI digests of genomic DR and DS DNAs and probes containing different P450 2C11 exonic sequences. AccI digests of genomic DNAs, isolated from the livers of DR and DS Dahl rats, were fractionated by gel electrophoresis in 0.8% agarose, the resulting DNA fragments transferred to nylon membranes and hybridized, at 65° C., to several [$^{32}$P] labeled DNA probes obtained by restriction endonuclease digestion of a rat P450 2C11 cDNA (1.8 kb). After several washes under high stringency conditions the membranes were exposed to X-ray film. The areas of the P450 2C11 gene recognized by the cDNA probes are as shown in FIG. 3. The size of the probes, the exons involved and the enzymes utilized for digestion of the P450 2C11 cDNA are described in the Specification.
Figure 5:
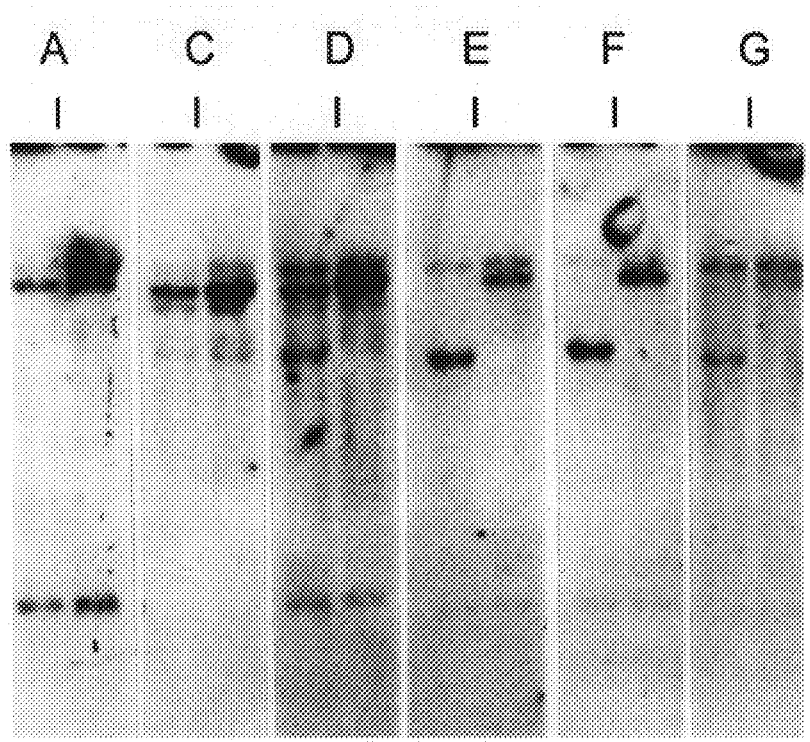

FIG. 5 Analysis of the hybridization patterns resulting from the interaction between KpnI digests of genomic DR and DS DNAs and probes containing different P450 2C11 exonic sequences. KpnI digests of genomic DNAs, isolated from the livers of DR and DS Dahl rats, were fractionated by gel electrophoresis, transferred to nylon membranes and hybridized to the indicated [$^{32}$P] labeled DNA probes exactly as described in FIG. 4 and in the Specification. The areas of the P450 2C11 gene recognized by the cDNA probes are as shown in FIG. 3. The size of the probes, the exons involved and the enzymes utilized for digestion of the P450 2C11 cDNA are described in the Specification.

Figure 6:
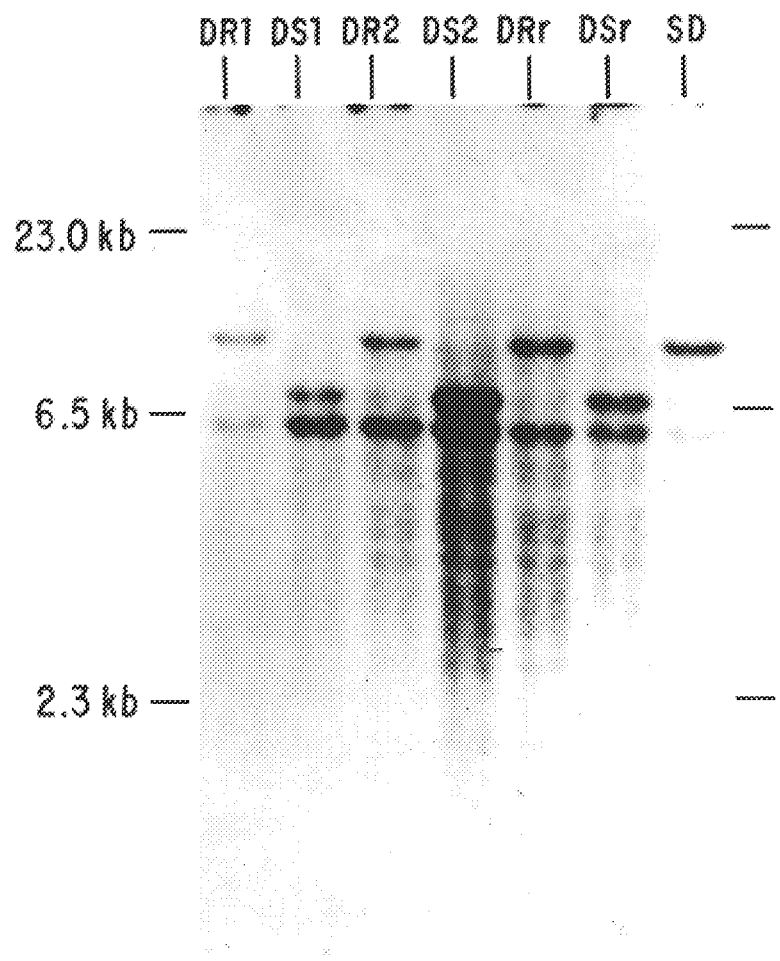

FIG. 6 Analysis of the hybridization Patterns resulting from the interaction between AccI digests of genomic DNA isolated from inbred (Rapp Strain). outbred (Brookhaven) Dahl and SD rats and an intronic, P450 2C11 specific DNA Probe. AccI digests of genomic DNAs isolated from inbred (Rapp), outbred (Brookhaven) DR and DS Dahl rats and from samples SD animals were electrophoresed in 0.8% agarose gels, transferred to nylon membranes and hybridized at 65° C. to a [$^{32}$P] DNA probe containing the 3.3 kb intron that separates exons 7 and 8 in the P450 2C11 gene (FIG. 3). After several washes under high stringency conditions the membranes were exposed to X-ray film.

DETAILED DESCRIPTION OF THE INVENTION

The invention provides an isolated gene encoding the rat P450 2C11 arachidonic acid epoxygenase, or a human homologue thereof, having a mutation associated with salt induced hypertension. In alternative embodiments, the human homologue is selected from the group consisting of P450 2C8, P450 2C18, P450 2C9/10 and P450 2C19. In another embodiment, the invention provides that the mutation is between exons 5 and 7 of the gene.

The invention also provides an isolated cell line expressing the epoxygenase encoded by the mutated gene. The invention also provides a non-human transgenic animal having a germ line insertion of the mutated gene and which functionally expresses the mutated epoxygenase and the hypertension phenotype. In one embodiment, the invention provides a method of screening a compound for efficacy in treating salt induced hypertension comprising administering the compound to such a non-human transgenic animal, and detecting an improvement in the animal's hypertension, thereby detecting a compound with efficacy in treating hypertension.

The invention also provides a method of screening a human subject for a genetic predisposition to salt induced hypertension comprising detecting a mutation in a human homologue of a rat P450 2C11 arachidonic acid epoxygenase gene which affects normal epoxygenase activity, the presence of the mutation indicating a predisposition to salt induced hypertension. The human homologue may be selected from the group consisting of P450 2C8, P450 2C18, P450 2C9/10 and P450 2C19. In one embodiment the mutation is between exons 5 and 7.

In one embodiment, the mutation may detected by detecting the presence of a restriction length polymorphism. In another embodiment, the mutation is detected by polymerase chain reaction amplification of genomic DNA using primers specific to the mutated gene or the normal gene. In another embodiment, the mutation is detected by detecting the presence of the mutated epoxygenase or the lack of presence of the normal epoxygenase in a biopsy of the subject's kidney.

The invention provides a method of treating salt induced hypertension in a human subject associated with a genetic mutation in a human homologue of the rat P450 2C11 arachidonic acid epoxygenase gene, comprising administering to the subject a functional metabolite, or analogue thereof, produced by the human homologue of the rat P450 2C11 arachidonic acid epoxygenase, thereby treating the salt induced hypertension. The human homologue may be selected from the group consisting of P450 2C8, P450 2C18, P450 2C9/10 and P450 2C19. In one embodiment, the mutation is between exons 5 and 7. In one embodiment, the metabolites are either 5,6-; 8,9-; 11,12-; or 14,15-cis-epoxyeicosatrienoic acid (EET), or a corresponding vic-dihydroxyeicosatrienoic acid (DHET).

The invention provides an isolated mutated rat P450 2C11 arachidonic acid epoxygenase, or a human homologue thereof, having a mutation associated with salt induced hypertension. The human homologue may be selected from the group consisting of P450 2C8, P450 2C18, P450 2C9/10 and P450 2C19. In one embodiment, the mutation is between exons 5 and 7 of the gene.

UTILITY

Hypertension affects 30–40 million Americans at an estimated annual cost of $10 billion per year in medical care and approximately $100 billion per year in lost productivity and disability. A predominant component of human hypertension is salt dependent. The identification of a gene defect linked to salt sensitive hypertension opens a variety of opportunities for the early detection, the prevention and the clinical management of human hypertension. The disclosure of the present invention provides the following uses to one with skill in the art.

Tools for Further Research in Cellular or Animal Models: With the present disclosure of the mutated epoxygenase gene, further cellular or animal research can be performed to characterize and treat salt induced hypertension. The production of cell lines or transgenic animals which express the mutated epoxygenase permit, for example, screening of compounds for efficacy in treating hypertension.

Early detection and prevention: The identification of the relevant genes with mutated sequences may be utilized to develop diagnostic kits for early detection of genetic predisposition to salt sensitive hypertension in the general population. A routine test would require minute blood samples and employ DNA amplification technology, such as PCR. Kits may include 10–15 mer oligonucleotide primers and the corresponding thermostable DNA polymerases. To simplify detection, sequences could be targeted to yield amplification only with, for example, wild type sequences or, alternatively, mutated sequences. The amplified sequence can be detected by selective hybridization to fluorescent, biotinylated and/or enzyme labeled DNA probes.

Management of human hypertension: Cytochrome P450 2C11 and its human homologues, Cytochromes P450 2C8 and 2C9/10 code for active arachidonic acid epoxygenases. The products of this reaction, the EETs and DHETs are excreted in human urine. Patients suffering from high blood pressure show altered levels of EET and DHETs in their urine. The unequivocal demonstration of a genetic link between this enzyme and salt sensitive hypertension indicates an antihypertensive role for the EETs and, therefore, potential therapeutical uses. Chemical synthesis can provide access to EET analogs with the chemical and metabolic stability required for clinical use.

Gene therapy: As with many current diseases that have been associated with a clearly defined genetic defect, gene replacement therapy provides the most direct and efficient means for clinical intervention.

TECHNIQUES

Experimental Animals

The polymorphic P450 2C11 gene is present in DNA samples obtained from several different, outbred, DR and DS animals, purchased over an 18 month time period. In outbred Dahl animals (Brookhaven strain), brother-sister mating is continued for a few generations prior to the introduction of foreign stocks (12). As a consequence this matting pattern, the fixation of genetic characteristics is, for the most part, avoided. Furthermore, to minimize the potential for salt independent hypertensive genotypes and, prior to isolation of genomic DNAs, individual DR and DS rats were selected based on their blood pressure response to high salt diets. While outbred and inbred strains have inherent advantages and disadvantages (12), outbred Dahl rats were utilized for the following additional reasons: a) to minimize the potential for P450 gene polymorphisms unrelated to phenotypic differences in salt sensitivity, b) when compared to age matched inbred DR animals, the magnitude of the salt-dependent increases in renal AA epoxygenase activity were significantly higher in outbred, Brookhaven, rats and, c) the lack of a reliable commercial source of inbred Dahl rats.

Identifying Human Homologues

The data disclosed herein establishes a polymorphic behavior (i.e., a mutation) between exons 5 and 7 in the rat Cytochrome P450 2C11 gene coding for an arachidonic acid epoxygenase. This genetic polymorphism has been associated with the salt-dependent development of hypertension in the Dahl rat model of salt sensitive hypertension. The identification of Cytochrome P450 2C11 as the altered rat gene indicates that members of the human Cytochrome P450 2C gene subfamily are similar in polymorphic structure in the human population. Furthermore, the higher the homology between a human P450 2C gene to this rat P450 2C11 gene, indicates that the gene is also involved in human salt sensitive hypertension. Therefore, the identification of the target gene in the human population is proved by identification of the rat Cytochrome P450 2C11 human homologues.

For a complete review of Cytochrome P450 homologies see Nelson et al., "The P450 Superfamily: Update on New Sequences, Gene Mapping, Accession Numbers, Early Trivial Names of Enzymes, and Nomenclature" *DNA and Cell Biology* 12:1–51 (1993). To establish homologies between a target sequence (rat Cytochrome P450 2C11) (SEQ ID NO:1) and the 2C gene subfamily human homologues, a computer search can be performed on any one of several of the gene data bases available. For example, the NIH GeneBank data base, maintained and supported by the NIH center for Biotechnology Information can be accessed by the Vanderbilt University mainframe DEC-VAX computer and the IntelliGenetics Molecular Biology Software System (5.4 UNIX).

Utilizing the FASTDB option of the IntelliGenetics Software and restricting the search to human homologues with 70% sequence identity with the rat Cytochrome P450 2C11, or the query "RATCYPM1 (1–1856)", resulted in the following:

| 1. | cyp 2C9/10 | approx. 77% coding sequence identity |
| 2. | cyp 2C18  | approx. 76% coding sequence identity |
| 3. | cyp 2C19  | approx. 73% coding sequence identity |
| 4. | cyp 2C8   | approx. 73% coding sequence identity |

Of these genes, 2C8 and P450 2C9/10, and to a lesser extent 2C18, are expressed in human kidneys. Since in human hypertension, as in the Dahl rat model, the kidneys are the key organ responsible for water and salt balance and, in most cases, hypertension can be directly linked to alteration in renal function, studies in the human population indicate these human homologues of the rat 2C1. Thus, after characterizing the genetic mutation of the rat 2C11 gene, one can then compare sequence alignments between the rat and the human homologues in the area of interest using the IntelliGenetics Software. Methods of charaterizing the mutation are discussed in greater detail below.

As used herein, "a" can mean one or more, depending upon the context in which it is used. As used herein, "isolated" means substantially free of the contaminants or other genes associated with the mutated gene or epoxygenase, or human homologues thereof, occurring in a natural environment. As used herein, "mutation" means a change in the nucleic acid sequence of the epoxygenase gene from the wild-type sequence which adversely affects the epoxygenase' enzymatic activity or regulation such that hypertension in the animal having the mutation can result.

As used herein, a "nucleic acid encoding" refers to a nucleic acid which has sufficient nucleotides surrounding the gene associated with salt induced hypertension to distinguish the nucleic acid from nucleic acids encoding non-related proteins. The specific length of the nucleic acid is a matter of routine choice based on the desired function of the sequence. For example, if one is making probes to detect the mutation, the length of the nucleic acid will be smaller, but must be long enough to prevent hybridization to the undesired background sequences. However, if the desired hybridization is to a nucleic acid which has been amplified, background hybridization is less of a concern and a smaller probe can be used. In general, such a probe will be between 10 and 100 nucleotides, and especially between 10 and 40 nucleotides in length. A "nucleic acid encoding" refers to such nucleotides encoding the rat P450 2C11 arachidonic acid epoxygenase, or human homologues thereof, having a mutation associated with salt induced hypertension.

Likewise, a mutated epoxygenase polypeptide encoded by the nucleic acids of the invention can be variable depending on the desired function of the polypeptide. While smaller fragments can work, generally to be useful for detecting the mutated protein, e.g., immunogenic, the polypeptide must be of at least 8 amino acids and not more than 10,000 amino acids. Thus, a fragment can be generated which is a truncated mutated epoxygenase isoform or otherwise modified form (as by amino acid substitutions, deletions, or additions). This recognizes that each mutated epoxygenase is encoded by a homologous gene that can undergo alternative intron/exon splicing.

It is apparent to one of skill in the art that nucleotide substitutions, deletions, and additions can be incorporated into the polynucleotides of the invention. However, such nucleotide substitutions, deletions, and additions should not substantially disrupt the ability of the polynucleotide to hybridize to one of the primer oligonucleotide sequences under hybridization conditions that are sufficiently stringent to result in specific hybridization.

The term "compound" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential biological activity by inclusion in screening assays described herein below.

The method of screening a subject by detecting the epoxygenase genetic mutation by PCR using "primers specific" is defined herein as the ability to detect the formation of hybrids between a probe nucleic acid (e.g., a nucleic acid which can include substitutions, deletions, and/or additions) and a specific target nucleic acid (e.g., a nucleic acid having the sequence), wherein the probe preferentially hybridizes to the specific target such that, for example, a band corresponding to a mutant epoxygenase homologue, or restriction fragment thereof, produced by hybridization permits amplification of the sequence target, which can be identified on a Southern blot, whereas a corresponding wild-type epoxygenase homologue is not identified or can be discriminated from a mutant epoxygenase homologue on the basis of signal intensity. Hybridization probes capable of specific hybridization to detect even a single-base mismatch can be designed according to methods known in the art and described in Maniatis et al. (1989) *Molecular Cloning: A Laboratory Manual*, 2nd Ed., Cold Spring Harbor Laboratory, Cold Spring Harbor, N.Y.; Berger and Kimmel (1987) "Guide to Molecular Cloning Techniques," *Methods in Enzymology*, Volume 152, Academic Press, Inc., San Diego, Calif.; Gibbs et al. (1989) *Nucleic Acids Res.* 17:2437; Kwok et al. (1990) *Nucleic Acids Res.* 18:999; and Miyada et al. (1987) *Methods Enzymol.* 154:94.

There are several methodologies available from recombinant DNA technology which can be used for detecting and identifying a genetic mutation responsible for salt induced hypertension. These include, for example, direct probing, polymerase chain reaction (PCR) methodology, restriction fragment length polymorphism (RFLP) analysis and single strand conformational analysis (SSCA). Additionally, the mutation can be detected by detecting the mutated epoxygenase or the lack of presence of the normal epoxygenase in a biopsy of the subject's kidney. However, any other known methods or later discovered methods can likewise be used to detect the mutations.

Detection of point mutations using direct probing involves the use of oligonucleotide probes which can be prepared synthetically or by nick translation. The DNA probes can be suitably labeled using, for example, a radioisotype label, enzyme label, fluorescent label, biotin-avidin label and the like for subsequent visualization in the example of Southern blot hybridization procedure. The labeled probe is reacted with a bound sample DNA, e.g., to a nitrocellulose sheet under conditions such that only fully complementary sequences hybridize. The areas that carry DNA sequences complementary to the labeled DNA probe become labeled themselves as a consequence of the reannealing reaction. The areas of the filter that exhibit such labeling can then be visualized, for example, by autoradiography. The labeled probe is reacted with a DNA sample bound to, for example, nitrocellulose under conditions such that only fully complementary sequences will hybridize. Tetra-alkyl ammonium salts bind selectively to A–T base pairs, thus displacing the dissociation equilibrium and raising the melting temperature. At 3M Me 4NCl this is sufficient to shift the melting temperature to that of G-C pairs. This results in a marked sharpening of the melting profile. The stringency of hybridization is usually 5° C. below the Ti (the irreversible melting temperature of the hybrid formed between the probe and its target sequence) for the given chain length. For 20mers the recommended hybridization temperature is 58° C. The washing temperatures are unique to the sequence under investigation and need to be optimized for each variant.

Alternative probing techniques, such as ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) is a technique that amplifies specific DNA sequences with remarkable efficiency. See (John Bell (1989) *Immunology Today* 10:351–355). Repeated cycles of denaturation, primer annealing and extension carried out with polymerase, e.g., a heat stable enzyme Taq polymerase, leads to exponential increases in the concentration of desired DNA sequences. Given a knowledge of the nucleotide sequence encoding the Cytochrome P450s, synthetic oligonucleotides can be prepared which are complementary to sequences which flank the DNA of interest. Each oligonucleotide is complementary to one of the two strands. The DNA is denatured at high temperatures (e.g., 95° C.) and then reannealed in the presence of a large molar excess of oligonucleotides. The oligonucleotides, oriented with their 3' ends pointing towards each other, hybridize to opposite ends of the target sequences and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. The resulting DNA can then be directly sequenced in order to locate any genetic alteration. Alternatively, it can be possible to prepare oligonucleotides that will only bind to altered DNA, so that PCR will only result in amplification of the DNA if the mutation is present. Following PCR, direct visualization or allele-specific oligonucleotide hybridization (Dihella et al. (1988) *Lancet* 1:497) can be used to detect the point mutation. Alternatively, an adaptation of PCR called amplification of specific alleles (PASA) can be employed; this uses differential amplification for rapid and reliable distinction between alleles that differ at a single base pair.

In yet another method, PCR can be followed by restriction endonuclease digestion with subsequent analysis of the resultant products. The point substitution or deletion of nucleotides in the mutated gene can destroy a nuclease restriction site. The destruction of a restriction endonuclease recognition site facilitates the detection of the epoxygenase mutation using RFLP analysis or by detection of the presence or absence of a polymorphic restriction site in a PCR product that spans the mutation.

In general, primers for PCR and LCR are usually about 20 bp in length and the preferable range is from 15–25 bp. Better amplification is obtained when both primers are the same length and with roughly the same nucleotide composition. Denaturation of strands usually takes place at 94° C. and extension from the primers is usually at 72° C. The annealing temperature varies according to the sequence under investigation.

For RFLP analysis, DNA is obtained, for example from the blood of the subject suspected of having a predisposition to salt induced hypertension and from a normal subject, is digested with restriction endonuclease(s), (e.g. AccI or KpnI) and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, DNA spanning an epoxygenase mutation that creates or removes a restriction site is detected by determining the number of bands detected and comparing this number to a wild-type reference allele.

Similar creation of additional restriction sites by nucleotide substitutions can be readily calculated by reference to the genetic code and a list of nucleotide sequences recognized by restriction endonucleases (*Promega Protocols and Applications Guide* (1991) Promega Corporation, Madison, Wis.). Single strand conformational analysis (SSCA) (Orita et al. (1989) *Genomics* 5:874–879 and Orita et al. (1990) *Genomics* 6:271–276) offers a relatively quick method of detecting sequence changes which can be appropriate in at least some instances.

PCR amplification of specific alleles (PASA) is a rapid method of detecting single-base mutations or polymorphisms (Newton et al. (1989) *Nucleic Acids Res.* 17:2503; Nichols et al. (1989) *Genomics* 5:535; Okayama et al. (1989) *J. Lab. Clin. Med.* 114:105, Sarkar et al. (1990) *Anal. Biochem.* 186:64; Sommer et al. (1989) *Mayo Clin. Proc.* 64:1361; Wu (1989) *Proc. Natl. Acad. Sci. (U.S.A.)* 86:2757; and Dutton et al. (1991) *Biotechniques* 11:700. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA can be used to specifically amplify one or more mutant epoxygenase homologues. Where such amplification is done on genetic material (or RNA) obtained from an individual, it can serve as a method of detecting the presence a mutation.

Similarly, a method known as ligase chain reaction (LCR) has been used to successfully detect a single-base substitution in a hemoglobin allele that causes sickle cell anemia (Baany et al. (1991) *Proc. Natl. Acad. Sci. (U.S.A.)* 88:189; R. A. Weiss (1991) *Science* 254:1992). LCR probes can be combined or multiplexed for simultaneously screening for multiple different mutations. Thus, one method of screening for mutant epoxygenase homologues is to multiplex at least one, and preferably all, LCR probes that will detect a mutant epoxygenase.

In performing diagnosis using any of the above techniques or variations thereof, it is preferable that several individuals are examined. These can include an unaffected parent, an affected parent, an affected sibling, an unaffected sibling as well as other perhaps more distant family members.

Having identified a genetic mutation in an epoxygenase gene that is associated with salt induced hypertension, it is possible, using genetic manipulation, to develop transgenic model systems and/or whole cell systems containing the mutated epoxygenase gene (or a portion thereof) for use, for example, as model systems for screening for drugs and evaluating drug effectiveness. Additionally, such model systems provide a tool for defining the underlying biochemistry of epoxygenase associated salt metabolism, which thereby provides a basis for rational drug design.

One type of cell system can be naturally derived. For this, kidney samples from an affected subject must be obtained in order to provide the necessary cells which can be permanently transformed into a lymphoblastoid cell line using, for example, Epstein-Barr virus. Once established, such cell lines can be grown continuously in suspension culture and can be used for a variety of in vitro experiments to study epoxygenase expression and processing. An alternative method for constructing a cell line is to genetically transfect the mutated gene into an established cell line of choice.

In yet a further use of the present invention, the mutated gene can be excised for use in the creation of transgenic animals containing the mutated gene. For example, an entire human homologue of the rat P450 2C11 can be cloned and isolated, either in parts or as a whole, in a suitable cloning vector (e.g., 1Charon35, cosmid, retrovirus or yeast artificial chromosome). The vector is selected based on the size of the desired insert and the ability to produce stable chromosome integration.

The mutant human epoxygenase gene, either in parts or in whole, can be transferred to a host non-human animal, such as a mouse. As a result of the transfer, the resultant transgenic non-human animal will express one or more mutant epoxygenase proteins.

Alternatively, one can design mini-genes encoding mutant P450 epoxygenase. Such mini-genes can contain a cDNA sequence encoding a mutant epoxygenase, preferably full-length, a combination of epoxygenase gene exons, linked to a downstream polyadenylation signal sequence and an upstream promoter (and preferably enhancer). Such a mini-gene construct will, when introduced into an appropriate transgenic host (e.g., mouse or rat), express an encoded mutant epoxygenase.

One approach to creating transgenic animals is to target a mutation to the desired gene by homologous recombination in an embryonic stem (ES) cell line in vitro followed by microinjection of the modified ES cell line into a host blastocyst and subsequent incubation in a foster mother (Frohman and Martin, *Cell* (1989) 56:145). Alternatively, the technique of microinjection of the mutated gene, or a portion thereof, into a one-cell embryo followed by incubation in a foster mother can be used. The successful delivery of a normal exogenous gene either to cells in culture (in vitro gene transfer) or to cells in a living organism (in vivo gene transfer, gene therapy) can include the use of viral based vectors (e.g., retroviruses, adenoviruses, and adeno-associated viruses) (Drumm, M. L. et al., *Cell* 62:1227–1233 (1990); Rosenfeld, M. A. et al., *Cell* 68:143–155 (1992); and Muzyczka, N., *Curr. Top. Micro. Immuno.* 158:97–129 (1992)) or such methods as lipofection, with either cationic liposomes (such as Lipofectin, LipofectAce, etc., (BRL) (Brigham, K. L. et al., *Amer. J. Respir. Cell and Mol. Biol.* 8:209–213 (1993)) or anionic liposomes. These lipofection methods can be targeted to a specific organ or cell type by methods known in the art, e.g., by site of injection or by including in the liposome structure components that direct the liposome to a specific target (e.g., Nicolau, C., et al., U.S. Pat. No. 5,017,359 (1991)). In addition, such viral vectors can be used to deliver the mutated gene to a developed animal and then used to screen for its presence (Mendelson et al. *Virology* 166:154–165; Wondisford et al. (1988) *Molec. Endocrinol.* 2:32–39 (1988)).

Site-directed mutagenesis and/or gene conversion can also be used to mutate an epoxygenase gene allele, either endogenous or transfected, such that the mutated allele is associated with salt induced hypertension.

The detection of a genetic mutation which predisposes an individual to salt induced hypertension permits various forms of therapy. One method of treatment comprises administering to the individual a functional metabolite, or analogue thereof, produced by the wild-type human homologue of the rat P450 2C11 epoxygenase. For example, the metabolites 5,6-; 8,9-; 11,12-; and 14,15-cis-epoxyeicosatrienoic acid (EETs), or their a corresponding hydrolization products, vic-dihydroxyeicosatrienoic acid (DHETs), can be administered to compensate for the individual's defective epoxygenase. These compounds can be obtained by selective epoxygenation as described in Korey, E. J., et al., *J. Am. Chem. Soc.*, 102:1433 (1980); Falck, J. R., and Manna, S., Tet. Lett., 23:1755 (1982).

Having detected the genetic mutation in the gene sequence coding for epoxygenase in an individual not yet showing overt signs of salt induced hypertension using the method of the present invention, it can be possible to employ gene therapy. The methods of gene therapy include the various forms of gene transfer discussed above in the context of creating transgenic animals or cell lines, such as by stem cell recombination, microinjection, viral vectors, and liposomes. The gene implanted can encode the normal epoxygenase, or encode an antisense strand of nucleic acid capable of inhibiting the mutated epoxygenase gene.

The modulation of the production of mutant epoxygenase proteins by methods that employ specific antisense polynucleotides includes polynucleotides that are complementary to all or part of a mutant sequence. Such complementary antisense polynucleotides can include nucleotide substitutions, additions, deletions, or transpositions, so long as specific hybridization to the relevant target sequence is achieved. Complementary antisense polynucleotides include soluble antisense DNA or RNA oligonucleotides which can hybridize specifically to a mutant epoxygenase DNA or mRNA species and prevent transcription of the mRNA species and/or translation of the encoded polypeptide (Ching et al. (1989) *Proc. Natl. Acad. Sci. (U.S.A.)* 86:10006–10010; Broder et al. (1990) *Ann. Int. Med.* 113:604–618; Loreau et al. (1990) *FEBS Letters* 274:53–56; WO91/11535; WO91/09865; WO91/04753; WO90/13641; and EP 386563). The antisense polynucleotides therefore inhibit production of the mutant epoxygenase polynucleotides.

Antisense polynucleotides can be produced from a heterologous expression cassette in a transfectant cell or transgenic cell or animal, such as a transgenic neural, glial, or astrocytic cell, preferably where the expression cassette contains a sequence that promotes cell-type specific expression (Wirak et al. (1991) *EMBO* 10:289). Alternatively, the antisense polynucleotides can comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA*, D. A. Melton, Ed. (1988), Cold Spring Harbor Laboratory, Cold Spring Harbor, N.Y.

In yet another aspect of the invention, having detected a genetic alteration in a gene sequence coding for epoxygenase, one can obtain samples of the altered protein from the same source. This protein can be derived from the tissues, such as kidney or liver, of a subject diagnosed as suffering from hypertension, or more preferably are produced by recombinant DNA methods or are synthesized by direct chemical synthesis on a solid support. Such polypeptides can contain an amino acid sequence of an epoxygenase mutant. The polypeptide material can be used to prepare antisera and monoclonal antibodies using, for example, the method of Kohler and Milstein ((1975) *Nature* 256:495–497). Such monoclonal antibodies could then form the basis of a diagnostic test.

The mutant epoxygenase polypeptides can also be used to immunize an animal for the production of polyclonal antiserum. For general methods to prepare antibodies, see *Antibodies: A Laboratory Manual*, Harlow and Lane (1988), Cold Spring Harbor Laboratory, Cold Spring Harbor, N.Y. For example, a recombinantly produced fragment of a mutant epoxygenase polypeptide can be injected into a mouse along with an adjuvant so as to generate an immune response. Immunoglobulins which bind the recombinant fragment with a binding affinity of at least $1 \times 10^7$ M-1 can be harvested from the immunized mouse as an antiserum, and can be further purified by affinity chromatography or other means. Additionally, spleen cells are harvested from the mouse and fused to myeloma cells to produce a bank of antibody-secreting hybridoma cells. The bank of hybridomas can be screened for clones that secrete immunoglobulins which bind the recombinantly produced fragment with an affinity of at least $1 \times 10^6$ M-1. More specifically, immunoglobulins that bind to the mutant epoxygenase polypeptide but poorly or not at all to a wild-type epoxygenase polypeptide are selected, either by pre-absorption with wild-type or by screening of hybridoma cell lines for specific idiotypes that bind the variant but not wildtype.

The nucleic acid sequences of the present invention capable of ultimately expressing the desired mutant epoxygenase polypeptides can be formed from a variety of different polynucleotides (genomic or cDNA, RNA, synthetic oligonucleotides, etc.) as well as by a variety of different techniques.

As stated previously, the DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Polynucleotides encoding a mutant epoxygenase polypeptide can include sequences that facilitate transcription (expression sequences) and translation of the coding sequences such that the encoded polypeptide product is produced. Construction of such polynucleotides is well known in the art and is described further in Maniatis et al. (1989) *Molecular Cloning: A Laboratory Manual*, 2nd Ed., Cold Spring Harbor Laboratory, Cold Spring Harbor, N.Y. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

E. coli is one prokaryotic host useful particularly for cloning the DNA sequences of the present invention. Other microbial hosts suitable for use include bacilli, such as Bacillus subtilus, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan promoter system, a betalactamase promoter system, or a promoter system from phage lambda. The promoters will typically control expression, optionally with an operator sequence, and have ribosome binding site sequences for example, for initiating and completing transcription and translation.

Other microbes, such as yeast, can also be used for expression. Saccharomyces is a preferred host, with suitable vectors having expression control sequences, such as promoters, including 3-phosphoglycerate kinase or other glycolytic enzymes, and an origin of replication, termination sequences etc. as desired.

In addition to microorganisms, mammalian tissue cell culture can also be used to express and produce the polypeptides of the present invention (see Winacker (1987) "From Genes to Clones," VCH Publishers, New York, N.Y.). Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, SFS insect cells, etc. Expression vectors for these cells can include expression control sequences, such as an origin of replication, a promoter, an enhancer (Quenn et al. (1986) *Immunol. Rev.* 89:49–68), and necessary information processing sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, recombinant vaculovirus, etc. The vectors containing the DNA segments of interest (e.g., encoding a mutant epoxygenase) can be transferred into the host cell by well-known methods, which vary depending on the type of cellular host. For example, cationic liposomes and/or calcium chloride transfection is commonly utilized for prokaryotic cells, whereas calcium phosphate treatment or electroporation can be used for other cellular hosts.

The method of detection lends itself readily to the formulation of test kits which can be utilized in diagnosis. Such a kit can comprise a carrier compartmentalized to receive in close confinement one or more containers wherein a first container can contain suitably labeled DNA probes. Other containers can contain reagents useful in the localization of the labeled probes, such as enzyme substrates. Still other containers can contain restriction enzymes, buffers etc., together with instructions for use.

Throughout this application various publications are referenced. The disclosures of these publications in their entireties are hereby incorporated by reference into this application in order to more fully describe the state of the art to which this invention pertains.

The examples herein are intended to illustrate but not limit the invention. While they are typical of those that might be used, other procedures known to those skilled in the art can be alternatively employed.

EXAMPLES

Animals: Male Sprague-Dawley rats (300–350 g body weight) or outbred, Brookhaven, male Dahl salt resistant and (Hsd:DR) and Dahl salt sensitive (Hsd:DS) rats (4–5 weeks old) were obtained from Harlam Sprague-Dawley Inc. (Indianapolis, Ind.). The Dahl animals utilized for these experiments were purchased between July 1992 and February 1994. Animals were maintained at 22° C. with alternating 12 hour cycles of light and dark and allowed free access to water and to standard rat chow containing 0.4% Na+ (w/w) (Purina Rat Chow, Purina Mills, St Louis, Mo.). Groups of DR and DS rats (260–300 g body weight) were fed a modified lab chow containing 8% NaCl (w/w)(Special Mix 5001-2-Purina Mills) for 12–18 days prior to MABP measurements. To confirm the Dahl animals DR and DS phenotypes, MABP were determined by the tail cuff method utilizing a Blood Pressure Analyzer Instrument (Model 178, IITC Life Science USA), at 30° C. and following the manufacturer's instructions. Animals were exposed to the 30° C. chamber for at least 30 minutes prior to measurements. Mean arterial blood pressure (MABP) was obtained after four consecutive readings whose values were within±5% of their mean. Only salt treated DR and DS rats with MABP of $\leq 125$ and $\geq 185$ mm of Hg, respectively, were utilized as the source of genomic DNAs.

Genomic DNA isolation and digestion: Anesthetized rats (Inactin, 150 mg/kg, 11. p.) were sacrificed by heart puncture, their livers immediately removed, freed of connective tissue and submerged in liquid $N_2$. Samples of frozen liver (1–2 g), pulverized in a dry ice cooled porcelain mortar, were transferred to a glass Teflon/ homogenizer and homogenized in 10 mM Tris-Cl buffer (pH 7.5) containing 10 mM NaCl and 1.5 mM $MgCl_2$. After a 10 minute centrifugation at 1,000×g, the nuclei pellet was collected, suspended in 10 mM Tris-Cl buffer (pH 7.5) containing 50 mM NaCl and 20 mM EDTA (buffer I) and centrifuged at 1,000×g for 10 minutes. The nuclei pellet was suspended by gentle mixing in buffer I containing 20 μg/ml of boiled pancreatic RNAase (Boehringer Mannheim, Indiana, Ind.), 100 μg/ml Proteinase K (Boehringer Mannheim) and 0.5% SDS (w/v). After 1 hour at 37° C., the concentration of proteinase K was raised to 300 μg/ml and the mixture incubated 1 hour at 50° C. and then extracted once with phenol (previously saturated with Tris-Cl pH 8.0), thrice with phenol/chloroform/isoamyl alcohol (25:24:1) and twice with chloroform/isoamyl alcohol (24:1). After centrifugation to affect phase separation, the water phases were dialyzed overnight at 4° C., first against $10^3$ volumes of 10 mM Tris-Cl buffer (pH 7.5) containing 50 mM NaCl and 1 mM EDTA and then, against 1 mM Tris-Cl buffer (pH 7.5) containing 10 mM NaCl and 0.1 mM EDTA. The sizes of the final DNA samples were >23 kb as determined by gel electrophoresis in 0.8% agar.

Nucleic acid hybridizations: Restriction endonucleases, obtained from New England Biolabs (Beverly, Mass.), Promega (Madison, Wis.) or Stratagene (La Jolla, Calif.), were incubated with the DNA samples (5–10 enzyme units/ μg of DNA) at 37° or 25° C. (SmaI) for 18 or 48 hours (KpnI) exactly as indicated by the enzyme's manufacturer.

The extent of digestion was assessed by gel electrophoresis (0.8% agar) and the reactions terminated after completion.

Digested samples of genomic DNA (10 μg DNA each) were loaded onto 0.8% agarose gels and electrophoresed (25–30Volts) in 40 mM Tris-acetate buffer (pH 8.0) containing 1 mM EDTA. After 18–20 hours, the gels were removed and the resolved DNA fragments transferred to nylon membranes (Zeta Probe Blotting Membranes, Bio-Rad, Richmond, Calif.) by capillary pressure for 24 hours. The nylon membranes were then dried under air, irradiated under UV light (Strata linker, Stratagene) and prehybridized, at 65° C., for 6–12 hours in 0.5M $Na_2HPO_4/NaH_2PO_4$ buffer (pH 7.2) containing 7% SDS and 1 mM EDTA. For hybridization, the [$^{32}$P]cDNA probes (0.25–1.8 kb) (approximately $2\times10^6$ cpm/ml) were dissolved in prehybridization buffer and incubated with the DNA containing membranes at 65° C. After 24 hours, the membranes were washed, at 65° C., twice with 40 mM $Na_2HPO_4/NaH_2PO_4$ buffer (pH 7.2) containing 5% SDS and 1 mM EDTA (30 minutes each) and twice with the same buffer but, containing 1% SDS. The membranes were air dried and exposed to the Kodak XAR-2 film at −70° C. The P450 2C11 cDNA utilized in these experiments was isolated from a poly(dT) primed male rat kidney cDNA library by standard screening procedures. This 1.8 kb cDNA contains the 3'-end polyadenylation tail and the complete P450 2C11 coding sequence (15,16).

DNA probes (between 0.25 to 1.8 kb) were labeled with [$\alpha$-$^{32}$P]dCTP (3 Ci/μmol) and a Random Primed DNA Labeling Kit (Boehringer Mannheim), according to the instructions provided. Unincorporated radioactivity was removed using Nick Columns (Pharmacia Biotechnology, Piscataway, N.J.) following the manufacture's protocol. Prior to labeling, DNA fragments obtained by restriction endonuclease cleavage of the P450 2C11 cDNA were purified by agarose gel electrophoresis and a QIAEX Gel Extraction Kit (Qiagen, Chatsworth, Calif.) as recommended by the manufacturer.

PCR amplification and cloning of genomic DNA fragments: For the amplification of the 3.3 kb intron separating exons 7 and 8 in the P450 2C11 gene (FIG. 3). The following 21-mer oligonucleotides were synthesized: 5'-ACAAACCTGCCTCATTTAGTG (SEQ ID NO:3) (sense, exon 7) (16,17) and 5'-GGGTCAAACTTCTCTGGATTA (SEQ ID NO:4) (antisense, exon 8) (16,17). The oligonucleotides (0.25 μM final concentration each) were dissolved in 10 mM Tris-Cl buffer (pH 8.3) containing 50 mM KCl, 3 mM $MgCl_2$ and 0.5 μg of genomic DNA isolated from either a DR or a DS Dahl rat. The following reagents then added, to the indicated final concentrations, sequentially: a mixture of dATP, dCTP, dGTP and dTTP (200 μM each), Ampli Taq DNA Polymerase (0.25 units) (Perkin Elmer, Norwalk, Conn.) and Perfect Match (0.5 units) (Stratagene). Amplification was achieved after 30 cycles of the following temperature program: 94° C., 1 minute; 49° C., 2 minutes; 72° C., 4 minutes. The 3.3 kb PCR product obtained by amplification of either the DR or DS DNA was purified utilizing a QIAEX Gel Extraction Kit (QIAEX) and ligated into a pCRII vector (TA Cloning Kit, Invitrogen, San Diego, Calif.) using a TaKaRa DNA Ligation Kit (Berkeley, Calif.). The presence of expected P450 2C11 exons 7 and 8 sequences was confirmed by partial sequence analysis of the insert 3' and 5' ends.

Example I

For these studies, commercially available, outbred, Brookhaven Dahl rats were utilized. After 12–18 days on a high salt food, the DR and DS phenotypes were confirmed by blood pressure measurements. Only salt loaded DR animals whose MABP were $\leq$125 mm Hg or DS animals with MABP $\geq$185 mm Hg were utilized. Samples of genomic DNA were isolated from the livers of several different groups of DR and DS animals, purchased over a 18 month time period. Genomic DNA samples were incubated with several restriction endonucleases, including BamHI, PsI EcoRI HindIII, XhaI, NcoI, AccI and KpnI.

After complete digestion, the products were size fractionated by agarose gel electrophoresis, transferred to nitrocellulose membranes and hybridized, under high stringency conditions, to [$^{32}$P] labeled full length cDNAs coding for P450s 2C11, 2C23 and 4A1. These P450 genes were targeted since; firstly, P450 2C11 and 2C23 are expressed in the rat kidney (25–27); secondly, P450 2C11 and 2C23 are known AA epoxygenases (24–26) and, thirdly, P450s 2C and 4A have been previously implicated in the development of hypertension in the SHR/WKY rat model of hypertension (1, 28, 29). Using the described experimental design, no restriction fragment length differences between DR and DS animals in their P450 2C23 or 4Al genes were detected. On the other hand, AccI and KpnI genomic DNA digests revealed that the DR and DS genotypes differed, markedly, in the structure of the 2C11 AA epoxygenase gene (FIG. 1).

Figure 1:
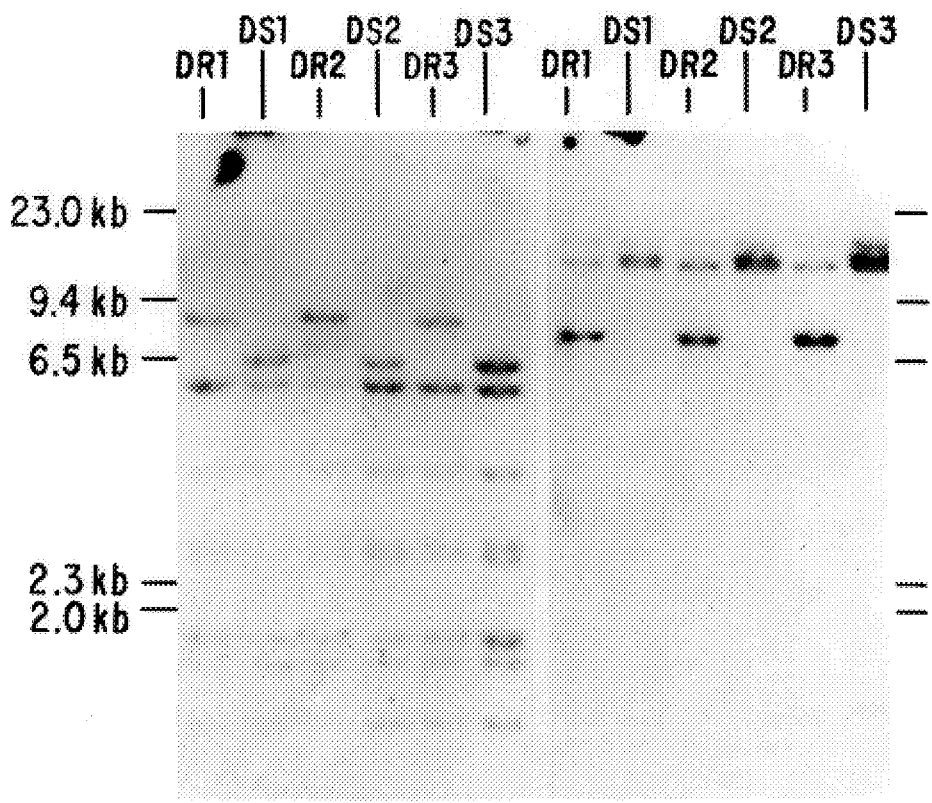
FIG. 1 Nucleic acid hybridization analysis of AccI and KpnI digests of genomic DNAs obtained from DR and DS Dahl rats. Genomic DNA samples, extracted from the livers of three different stocks of DR and DS rats, were incubated with AccI and KpnI as indicated in the Examples. The resulting DNA fragments were electrophoresed in 0.8% agarose gels, transferred to nylon membranes, hybridized, at 65° C., to a [$^{32}$P] labeled cDNA coding for rat P450 2C11 (1.8 kb) and, after several washes under high stringency conditions the membranes were exposed to X-ray film. The migration of DNA markers of known sizes (in kilobase pairs) is indicated at left.

An analysis of the AccI digestion and P450 2C11 hybridization data in FIG. 1 shows that: 1) the AccI restriction patterns for the P450 2C11 gene in DR and DS rats are complex and show fragments ranging in size from approximately 9 to 1 kb; 2) a P450 2C11 8.1 kb gene fragment, present in all the DR DNA samples so far studied, missing from the DS DNA digests, has been replaced by a DS specific 6.5 kb fragment; 3) the 8.1 kb (DR) to 6.5 kb (DS) replacement is the only apparent structural difference between the P450 2C11 genes associated with the DR and DS genotypes; 4) this, genotype specific, polymorphic behavior of the 2C11 gene is present in several DNA samples collected, over an 18 month time period, from animals selected by their MABP responses to dietary salt loading; 5) the AccI polymorphic 8.1 and 6.5 fragments are completely segregated between the DR and DS genotypes, respectively (none of the DR or DS samples analyzed shows both fragments coexisting in single DR or DS DNA sample); and 6) the apparent precursor-product relationship between the two polymorphic 2C11 fragments suggest that gene deletion can be responsible for the different P450 2C11 genotypes.

The P450 2C11 hybridization patterns generated after digestion of genomic DNAs isolated from DR and DS rats with KpnI are less complex than those obtained with AccI (FIG. 1). The KpnI digests show four 2C11 positive fragments that range in size from approximately 12 to 7 kb (FIG. 1). Importantly, a 7.5 kb fragment, present in all the DR samples so far analyzed, is missing from the DS digests and it has been replaced by a new, DS specific, 11 kb fragment (FIG. 1). These KpnI restriction fragment size differences are the only P450 2C11 gene differences between the DR and DS animals that are evident in FIG. 2. As with the AccI digests, the KpnI polymorphism is present in several DNA samples collected, over an 18 month time period, from DR and DS animals selected by their MP response to dietary salt loading. In 8 different samples of genomic DS and DR DNAs analyzed, there has been no observation of a DR or a DS DNA sample that, after KpnI digestion, contains both the 11 and the 7.5 kb fragments. The complete segregation of polymorphic AccI and KpnI restriction fragments between DR and DS genotypes (FIG. 1) suggest that salt sensitive, hypertensive DS animals, are homozygous with respect to the 2C11 gene locus. The data in FIG. 1 also indicates that the P450 2C11 gene polymorphism is likely due to loss or deletion of a DNA segment. This gene deletion would then result in the creation of a 6.5 kb AccI fragment and the loss of a KpnI site.

Example II

Figure 2:
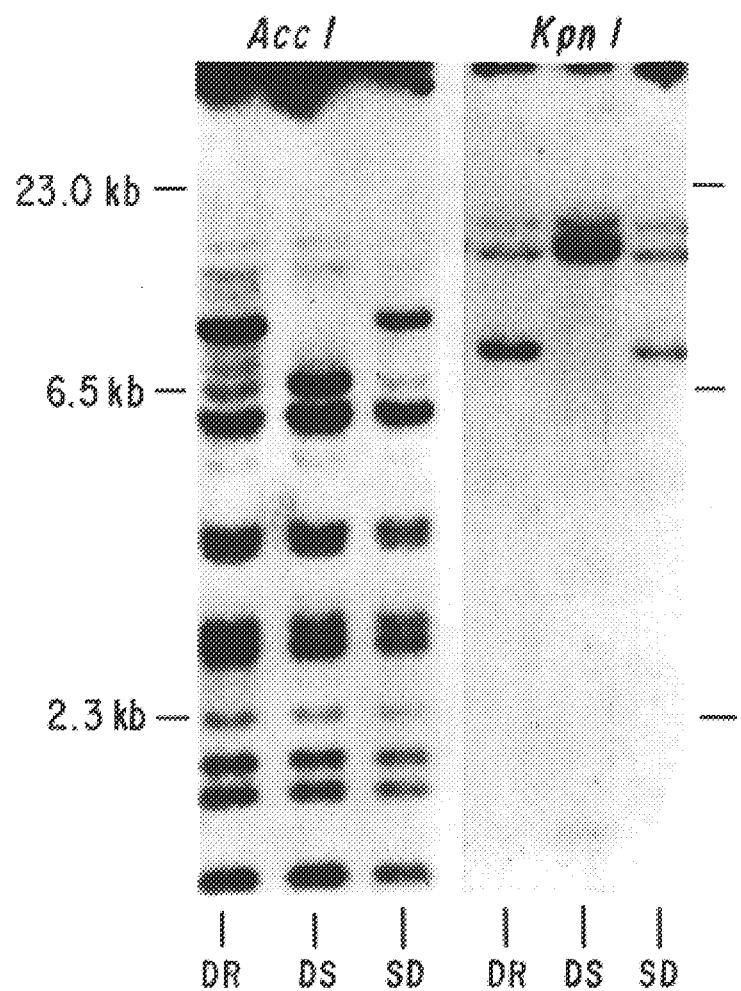
FIG. 2 Nucleic acid hybridization analysis of AccI and KpnI digests of genomic DNA isolated from SD and from DR and DS Dahl rats. Genomic DNA samples, extracted from the livers of SD, DR and DS rats, were incubated with AccI and KpnI until complete digestion as indicated in the Examples. After electrophoresis in 0.8% agarose gels, the resulting DNA fragments were transferred to nylon membranes, hybridized at 65° C. to a [$^{32}$P] labeled cDNA coding for rat P450 2C11 (1.8 kb), and after several washes under high stringency conditions the membranes were exposed to X-ray film.

To further establish a relationship between salt response phenotypes and P450 2C11 genotypes, as well as to determine the relationship of the P450 2C11 DR and DS genotypes to that of the wild type, SD population, genomic DNAs, isolated from DR, DS and SD rat livers, were digested with AccI and KpnI, fractionated by gel electrophoresis and hybridized, under high stringency, to the P450 2C11 cDNA probe. As shown in FIG. 2, SD and DR animals share common P450 2C11 genotypes. In contrast, salt sensitive DS animals show a different, altered, P450 2C11 AA epoxygenase gene. Based on these results, one can conclude that a mutated P450 2C11 gene is present only in the DS genotype.

Example III

To identify areas of the gene responsible for its DR/DS polymorphism, several exonic DNA probes were generated by restriction endonuclease digestion of a P450 2C11 cDNA. The cDNA utilized for these experiments was isolated from a rat liver oligo(dT) primed cDNA library, extends 1870 bp from the 3'-end poly-adenylation tail, contains the full coding sequence for P450 2C11 (15–17) and, has two AccI sites (at nucleotides 198 and 1543) and a single KpnI site (at nucleotide 1170) (15–17). The cDNA probes generated, their nucleotide position relative to the cDNA 5' end and, the restriction enzymes utilized to generate them were as follows: A. PstI (5'-end)-HincII(336); B. PstI(5'-end)-HincII (875); C. HincII (336)-AvaI (799); D. HincII (336)-KpnI (1170); E. AvaI(799)-AvaI(XhoI) (3' end); F MspI (1022)-XhoI (3'-end); G. BamHI (1024)-XbaI (1256); and, H. AccI (1543)-XhoI (3'-end).

When AccI digests of DR and DS genomic DNA were analyzed, under high stringency conditions, with each DNA-probe, it was observed that the P450 2C11 polymorphism was only evident with probes containing sequences from exons 7 and 8 (probes D, F and G; FIGS. 3 and 4). On the other hand, no 2C11 polymorphism could be detected when the AccI digests were hybridized to probes A, B and H. (FIGS. 3 and 4).

The results obtained with the KpnI digests were similar, i.e., the polymorphism was evident only with those DNA probes containing sequences from exons 7 and 8 of the 2C11 gene. (FIGS. 3 and 5). The 3.3 kb intron between exons 7 and 8 of the 2C11 gene (FIG. 3) was cloned by PCR amplification of genomic DR and DS DNAs as described. Restriction endonuclease analysis demonstrated the lack of AccI and KpnI sites in this 2C11 gene intron. Based on these results, as well as, on the sizes of the DR and DS AccI and KpnI specific fragments, one can conclude that the P450 2C11 mutation in the DS rats is localized downstream from exon 5 and upstream from the KpnI site in exon 8 (nucleotide 1170 from the 5'-end of the 2C11 cDNA) (15–17). This area of the gene is approximately 20 kb long and contains exons 6 and 7 (FIG. 3).

Example IV

The high degree of sequence homology among the members of the P450 450 2 gene family and, in particular, among 2C subfamily isoforms, complicates the interpretation of nucleic acid hybridization data (15). For example, cross-hybridization between the 2C11 cDNA and additional 2C subfamily homologous exonic sequences could be responsible for the complexity of the AccI digest hybridization patterns in FIG. 1. To demonstrate, unequivocally, that the genetic polymorphism documented in the DR and DS animals was associated with the P450 2C11 gene, a 2C11 specific probe was generated by PCR amplification of the 3.3 kb intron that separates exons 7 and 8 (FIG. 3). As primers we synthesized two oligonucleotides (21 mer, each, sense and antisense) containing parts of the published sequence for exon 7 (starting 35 bases upstream from the exon's 3'-end exon/intron boundary) (16) and exon 8 (starting 20 bases downstream for the exon's 5'-end exon/intron boundary) (16).

PCR amplification of genomic DR and DS DNA yielded, with both templates, a 3.3 kb DNA fragment (16). Cloning into a pCRII vector followed by partial sequence analysis demonstrated that both PCR products did indeed contained the expected 2C11 sequences at their 3' and 5' ends (approximately 40 to 50 bases at each end). The DR and DS 3.3 kb fragments, containing P450 2C11 specific intronic sequences, were labeled with [$\alpha$-$^{32}$P] dCTP and utilized to probe AccI digests of genomic SD, DR and DS DNAs.

This probe was also analyzed with AccI digests of genomic DNA isolated from the livers of DS and DR inbred (Rapp) Dahl rats (12). As shown in FIG. 6, the P450 2C11 specific intronic fragments hybridized to the previously described 8.1 and 6.5 kb AccI fragments, typical of the DR and DS genotypes. Importantly, these 2C11 genotypic differences were also evident in the inbred strain of Dahl rats (Rapp) (FIG. 6). Furthermore, the P450 2C11 genotype identity between SD and DR animals was also corroborated by the P450 2C11 specific probe (FIG. 6). Therefore, permitting the conclusion that the described genotype differences between the DR and DS animals is due to differences in the structure of the gene coding for a P450 2C11 arachidonic acid epoxygenase and that, DS rats contain a mutated P450 2C11 gene.

REFERENCES

1. McGiff, J. C. (1991) *Ann. Rev. Pharmacol. Toxicol.*, 31: 339–369 and references therein.
2. Smith, W. L. (1992) *Am. J Physiol.*, 263: F181–F191 and references therein.
3. Capdevila, J. H., Falck, H. R. and Estabrook, R. W. (1992) *FASEB J.*, 6: 731–736 and references therein.
4. Oliw, E. H. (1994) *Prog. Lipid Res.*, 33: 329–354 and references therein.
5. Capdevila, J. H., Wei, S., Yang, J., Jacobson, H. R., Falck, J. R., Guengerich, F. P. and DuBois, R. N. (1992) *J Biol. Chem.*, 267: 21720–21726.
6. Jacobson, H. R., Corona, S., Capdevila, J. H., Chacos, N, Womack, A., and Falck, J. R. (1984) in *Prostaglandins and Membrane Ion Transport*, (Braquet, P., Garay, R. P., Frolich, J. C. and Nicosia, S., Eds.) Raven Press, New York. 311–318.
7. Romero, M. F., Madhun, Z., Hopfer, U. and Douglas, J. G. (1990) in Advances in *Prostaglandin, Thromboxane and Leukotriene Research*, (Sammuelson, B., Ramwell, P., Paoletti, R. and Folco, G., Eds.) Raven Press, New York. 205–208.
8. Hirt, D. L., Capdevila, J. H., Falck, J. R., Breyer, M. and Jacobson, H. R. (1989) *J. Clin. Invest.*, 84: 1805–1812.
9. Schlondorff, D., Petty, E., Oates, J. A. and Levine, S. D. (1987) *Am. J. Physiol.*, 253: F464–F470.

10. Katoh, T., Takahashi, K., Capdevila, J. H., Karara, A., Faick, J R., Jacobson, H. R. and Badr, K. F. (1991) *Am. J. Physiol.*, 261: F578–F586.
11. Catella, F., Lawson, J. A., Fitzgerald, D. J. and Fitzgerald, G. A. (1990) *Proc. Natl. Acad. Sci (USA)*, 87: 5893–5897.
12. Rapp, J. P. (1982) *Hypertension*, 4: 753–763 and references therein.
13. Dahl, L. K., Heine, M. and Thompson, K. (1974) *Circulation Res.*, 34: 94–101.
14. Makita, K., Takahashi, K., Karara, A., Jacobson, H. R., Faick, J. R. and Capdevila, J. H. (1994) *J. Clin. Invest.*, (in Press).
15. Nelson, D. R., Kamataki, T., Waxman, D. J., Guengerich, F. P., Estabrook, R. W., Feyereisen, R., Gonzalez, F. J., Coon, M. J., Gunsalus, I. C., Gotoh, O., Okuda, K. and Nebert, D. W. (1993) *DNA and Cell Biol.*, 12: 1–51 and references therein.
16. Morishima, N., Yoshiaka, H., Higashi, Y., Sogawa, K and Fujii-Kuriyama, Y. (1987) *Biochemistry*, 26: 8279–8285.
17. Yoshiaka, H., Morahashi, K., Sogawa, K., Miyata, T., Kawajiri, K., Hirose, T., FujiiKuriyama, Y. and Omura, T. (1987) *J. Biol. Chem.*, 262: 1706–1711.
18. Gonzalez, F. J. (1989) *Pharmacol. Revs.*, 40: 243–286 and references therein.
19. Waxman, D. J. (1984) *J. Biol. Chem.*, 259: 15481–15490.
20. Lund, J., Zaphiropoulos, P. G., Mode, A., Warner, M. and Gustafsson, J. A. (1991) *Advances in Pharmacology*, 22: 325–354 and references therein.
21. Legraverend, C., Mode, A., Wells, T., Robinson, I. and Gustafsson, J. A. (1992) *FASEB J.*, 6: 711–718 and references therein.
22. Soucek, P. and Gut, I. (1992) *Xenobiotica*, 22: 83–103 and references therein.
23. Em, Y., Chijiwa, C. and Omura, T. (1990) *Proc. Natl. Acad. Sci.* (USA), 87: 97469750.
24. Capdevila, J. H., Karara, A., Waxman, D. J. Martin, M. V., Falck, J. R. and Guengerich, F. P. (1990) *J. Biol. Chem.*, 265: 10865–10871.
25. Karara, A., Makita, K., Jacobson, H. R., Falck, J. R., Guengerich, F. P., DuBois, R. N. and Capdevila, J. H. (1993) *J. Biol. Chem.*, 268: 13565–13570.
26. Imaoka, S., Wedlund, P. J., Ogawa, H., Kimura, S., Gonzalez, F. J. and Kim, H. (1993) *J. Pharmacol. Exp. Ther.*, 267: 1012–1016.
27. Zaphiropoulos, P. G. (1990) *Biochem. Biophys. Res. Commun.*, 180: 645–651.
28. Schenkman, J. B., Thummel, K. E. and Favreau, L. V. (1989) *Drug Metabolism Rev.*, 20: 557–584 and references therein.
29. Iwai, N. and Inagarni, T. (1990) *Hypertension* 17: 161–169.
30. Matsukawa, N., Nonaka, Y., Higaki, J., Nagano, M., Mikami, H., Ogihara, T. and Okamoto, M. (1993) *J. Biol. Chem.*, 268: 6117–6121.
31. Hua, J., Frederick, J., Kaskel, J., Juno, C., Moore, L. C. and McCaughran, A. J. (1990) *Am. J. Hypertens.*, 3: 268–273.
32. Sinaiko, A. R. (1991) *Am. J. Hypertens.*, 4: 76–80.
33. Nishi, A., Bertorello, A. M. and Aperia, A. (1992) *Acta Physiol. Scand.*, 144: 236–267.
34. Herrera, V. L. M. and Opazo-Ruiz, N. (1990) *Science* 249:1023–1026.
35. Simonet, L., Lezin, E. and Kurtz, T. W. (1991) *Hyperiension*, 18: 686–693.
36. Rapp, J. P. and Dahl, L. K. (1976) *Biochemistry*, 15: 1235–1242.
37. Rapp, J. P., Wang, S. M. and Dene, H. (1989) *Science*, 243: 542–544.

What is claimed is:

1. An isolated nucleic acid encoding the rat P450 2C11 arachidonic acid epoxygenase, having a mutation which results in salt induced hypertension in rats.

2. The nucleic acid of claim 1, wherein the mutation is located between exons 5 and 7.

3. An isolated cell comprising the nucleic acid of claim 1, wherein said cell expresses the rat P450 2C11 archidonic acid epoxygenase encoded by said nucleic acid.

* * * * *

UNITED STATES PATENT AND TRADEMARK OFFICE
CERTIFICATE OF CORRECTION

| | | |
|---|---|---|
| PATENT NO. | : 5,834,293 | Page 1 of 1 |
| APPLICATION NO. | : 08/314601 | |
| DATED | : November 10, 1998 | |
| INVENTOR(S) | : Capdevila et al. | |

It is certified that error appears in the above-identified patent and that said Letters Patent is hereby corrected as shown below:

Please replace the first paragraph of the specification, which appears on page 1, column 1, line 5 with the following:

Government Support Clause

This work was supported in part by United States Public Health Services Grant NIHDK 38226 and NIHGM 37922. The United States Government has rights in the invention.

Signed and Sealed this
Twelfth Day of April, 2011

David J. Kappos
*Director of the United States Patent and Trademark Office*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 2140 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
CATGAGCTAT  CACTGCATTG  TATCCATATT  CCACAGAGTT  TAGCACCCAG  GTATGGCATA    60

ATAATAATAA  ATCTTATTGT  AAATTGGAGA  AAGGACAGAT  TTAGGTTCCC  TTTTACAGAA   120

GCCCAGGAGG  CACAGCCTTA  TTTGAAAGAA  AAAGCAACTG  GCATAAAGTG  GTGGATTATG   180

TCACTTTGTG  TGATGGTAGT  AATCACTTAT  TATGTAAACC  AGAGTATCTA  TTGCACACCT   240

TAAATGTAGG  CAATAAAAGT  AAAACGGGAA  GCAGTAAAAA  ATACTGTAGA  GGCCACCGCC   300

ATGCCATCCA  GACTGAGGAA  GACCCGGAAA  TTCCGGGGCC  ACGTGAGCCA  CAGCCACGGT   360

CGCATTGGTA  AGCACCGCAA  GCACCCAGGA  GGCCGCGGGA  ATGCTGGAGG  CACGCAATTA   420
```

-continued

| | | | | | |
|---|---|---|---|---|---|
|CCACGGATCA|ACTTTGACAA|ATATCATCCT|GGTTACTTTG|GCAAAGTCGG|CATGAGTCAT|480|
|TACCACTTGA|AGAGGAGCCA|GAGCTTCTGC|CCAACTGTCA|ACCTGGATAA|ATTATGGACG|540|
|TTGGTCAGCC|AGCAGACACG|TGTCAATGCA|GCAAAAACA|AGAGTGGAGC|TGCTCCCATC|600|
|ATTGATGTTT|TTCCAATCAG|GCTACTACAA|GTTCTGAGGA|AGGGGAAGCT|TCCTAAGCAA|660|
|CCTGTCATCG|TGAAGGCCAA|ATTCTTCAGC|AGAAGAGCTG|AAGAGAAGAT|AAAGGGTGTT|720|
|GGAGGTGCCT|GTTCTGGTGG|CTTAAAGTCA|CTTCAGAGGT|TAATTAAATG|CAAACATTTT|780|
|CCATGAAAAA|AAAATATTGT|AGAAATGAAT|TAGCAGTTAA|GAGCACTGGC|TGCTCTTCCA|840|
|GAGAATCTCA|CCTGTTTGTA|ACTCTAGTTC|CACAGCTTCT|GAGACCCTCA|CACAGACATA|900|
|CATGGAGGCA|AAACAGGGTT|GAACTATAAG|ATAAAAACC|AGTGTGGTGT|ATATCCAACT|960|
|GTTATTCCCG|CATTCTCTGC|TAAAAGGGCT|TTGTATGCAA|AAGGTACCTT|TATTATATGA|1020|
|GCTAATTACA|TGACTTAATT|GGTGAGTAAT|CATGGCTAAT|ATTACTATAG|CATGCTAAAG|1080|
|GAAGTATCCT|AACCAACTGG|GAAGATTTAC|TGTGTAAACC|ATTACTTTAT|TTACAAGTAT|1140|
|ATGGTTTACC|TTCACTGCTA|AAACTCAGTC|TAAGAATGCA|ATGATCTTTG|GATAACATGA|1200|
|TTTACTAGAT|TAGCCCTGAG|TTTAGATTGT|ATGTTGAAAC|TCTCTGGGGT|ATTTGAAAAA|1260|
|AAGAAAAAAA|AAGACAGTAA|ATGAGTGATA|TGGGAGGGGG|TGCCTTAGTT|GGCTCATGCT|1320|
|GAGGCACACC|TGCCCACATC|TCCCCCTTCT|CCCCTCCCCC|GAGGTACCAG|CCATATATGG|1380|
|GTCTAGTATA|AAAGAGAGCT|TATTTGGAGG|CATGGGAAAG|GGGGTTGAGA|AGGAAGTTGA|1440|
|GGCAGAGAAA|GAGAAGTACA|GAGAGAGAGA|GAGGAAAGAA|AGGAGAAGAG|GCAGGCCAGG|1500|
|AATATGTGGA|GAGGATGAGA|GAGGACTTGA|GAGGAAAGAG|AGAGAGGGTA|AGAGGGACTG|1560|
|AGGGAGAGGG|AGAGAAGGAG|AGAAGGAGAG|AGGGAGAGAG|AGGGAGAGAG|AGAGAGGAAG|1620|
|GTTAGAGAGC|AAAGAGAGGC|TAGTCATTTT|TATGGCAAGC|CAGGCTCTTG|TCTGGATGTT|1680|
|GCTATGTAAC|AGTTGGGTAG|AGCCAAGAAG|GAATGCTAAG|AAGCTAACTT|TGGGTCCCAC|1740|
|CCCTGGTTAG|TTACACAGAT|TTGTGGTAGT|AGAAAGAGGA|AGAACAGTTT|TCACTTGTGT|1800|
|ATTTTAACAG|GTCAGGGTCC|ACAAAGAAGA|AATATTAAAG|CATATCTAGT|TGATTGGTCA|1860|
|CTTAGGTATC|AGAAGCTCAT|GTTGAATTGG|CAGCTAGCTA|GCATTATAAA|AGTCCTGGAC|1920|
|AGCAAGCTCA|CAGGAGTCTC|CCTGAGGAAG|GCTGCCATGG|ATCCAGTCCT|AGTCCTGGTG|1980|
|CTCACTCTCC|TCTCTCTGCT|TCTCCTCTCA|CTCTGGAGAC|AGAGCTTTGG|GAGAGGGAAG|2040|
|CTCCCTCCTG|GTCCAACACC|TCTCCCAATC|ATTGGAAACA|CCCTTCAGAT|ATATATGAAG|2100|
|GACATCGGCC|AATCAATAAA|AAAGGTAAGT|GTTTTTTAAG| | |2140|

( 2 ) INFORMATION FOR SEQ ID NO:2:

( i ) SEQUENCE CHARACTERISTICS:
        ( A ) LENGTH: 500 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Asp Pro Val Leu Val Leu Val Leu Thr Leu Ser Ser Leu Leu Leu
 1               5                  10                  15

Leu Ser Leu Trp Arg Gln Ser Phe Gly Arg Gly Lys Leu Pro Pro Gly
            20                  25                  30

Pro Thr Pro Leu Pro Ile Ile Gly Asn Thr Leu Gln Ile Tyr Met Lys
        35                  40                  45
```

```
Asp Ile Gly Gln Ser Ile Lys Lys Phe Ser Lys Val Tyr Gly Pro Ile
     50                  55                  60

Phe Thr Leu Tyr Leu Gly Met Lys Pro Phe Val Val Leu His Gly Tyr
 65                  70                  75                  80

Glu Ala Val Lys Glu Ala Leu Val Asp Leu Gly Glu Glu Phe Ser Gly
                 85                  90                   95

Arg Gly Ser Phe Pro Val Ser Glu Arg Val Asn Lys Gly Leu Gly Val
                100                 105                 110

Ile Phe Ser Asn Gly Met Gln Trp Lys Glu Ile Arg Arg Phe Ser Ile
            115                 120                 125

Met Thr Leu Arg Thr Phe Gly Met Gly Lys Arg Thr Ile Glu Asp Arg
        130                 135                 140

Ile Gln Glu Glu Ala Gln Cys Leu Val Glu Glu Leu Arg Lys Ser Lys
145                 150                 155                 160

Gly Ala Pro Phe Asp Pro Thr Phe Ile Leu Gly Cys Ala Pro Cys Asn
                165                 170                 175

Val Ile Cys Ser Ile Ile Phe Gln Asn Arg Phe Asp Tyr Lys Asp Pro
            180                 185                 190

Thr Phe Leu Asn Leu Met His Arg Phe Asn Glu Asn Phe Arg Leu Phe
            195                 200                 205

Ser Ser Pro Trp Leu Gln Val Cys Asn Thr Phe Pro Ala Ile Ile Asp
210                 215                 220

Tyr Phe Pro Gly Ser His Asn Gln Val Leu Lys Asn Phe Phe Tyr Ile
225                 230                 235                 240

Lys Asn Tyr Val Leu Glu Lys Val Lys Glu His Gln Glu Ser Leu Asp
                245                 250                 255

Lys Asp Asn Pro Arg Asp Phe Ile Asp Cys Phe Leu Asn Lys Met Glu
            260                 265                 270

Gln Glu Lys His Asn Pro Gln Ser Glu Phe Thr Leu Glu Ser Leu Val
        275                 280                 285

Ala Thr Val Thr Asp Met Phe Gly Ala Gly Thr Glu Thr Thr Ser Thr
    290                 295                 300

Thr Leu Arg Tyr Gly Leu Leu Leu Leu Leu Lys His Val Asp Val Thr
305                 310                 315                 320

Ala Lys Val Gln Glu Glu Ile Glu Arg Val Ile Gly Arg Asn Arg Ser
                325                 330                 335

Pro Cys Met Lys Asp Arg Ser Gln Met Pro Tyr Thr Asp Ala Val Val
            340                 345                 350

His Glu Ile Gln Arg Tyr Ile Asp Leu Val Pro Thr Asn Leu Pro His
        355                 360                 365

Leu Val Thr Arg Asp Ile Lys Phe Arg Asn Tyr Phe Ile Pro Lys Gly
    370                 375                 380

Thr Asn Val Ile Val Ser Leu Ser Ser Ile Leu His Asp Asp Lys Glu
385                 390                 395                 400

Phe Pro Asn Pro Glu Lys Phe Asp Pro Gly His Phe Leu Asp Glu Arg
                405                 410                 415

Gly Asn Phe Lys Lys Ser Asp Tyr Phe Met Pro Phe Ser Ala Gly Lys
            420                 425                 430

Arg Ile Cys Ala Gly Glu Ala Leu Ala Arg Thr Glu Leu Phe Leu Phe
        435                 440                 445

Phe Thr Thr Ile Leu Gln Asn Phe Asn Leu Lys Ser Leu Val Asp Val
    450                 455                 460

Lys Asp Ile Asp Thr Thr Pro Ala Ile Ser Gly Phe Gly His Leu Pro
465                 470                 475                 480
```

```
Pro Phe Tyr Glu Ala Cys Phe Ile Pro Val Gln Arg Ala Asp Ser Leu
            485                 490                 495

Ser Ser His Leu
            500
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ACAAACCTGC CTCATTTAGT G          21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GGGTCAAACT TCTCTGGATT A          21